US010898295B1

United States Patent
Alshehri

(10) Patent No.: US 10,898,295 B1
(45) Date of Patent: Jan. 26, 2021

(54) ENDODONTIC POINT CONTAINING ULTRASONIC DEFORMABLE MATERIAL

(71) Applicant: KING SAUD UNIVERSITY, Riyadh (SA)

(72) Inventor: Mohammed Abdullah Alshehri, Riyadh (SA)

(73) Assignee: KING SAUD UNIVERSITY, Riyadh (SA)

(*) Notice: Subject to any disclaimer, the term of this patent is extended or adjusted under 35 U.S.C. 154(b) by 0 days.

(21) Appl. No.: 16/657,985

(22) Filed: Oct. 18, 2019

(51) Int. Cl.
*A61C 5/50* (2017.01)
*B06B 3/00* (2006.01)
*A61K 6/15* (2020.01)
*A61K 6/54* (2020.01)
*A61K 6/69* (2020.01)

(52) U.S. Cl.
CPC ............ *A61C 5/50* (2017.02); *A61K 6/15* (2020.01); *A61K 6/54* (2020.01); *A61K 6/69* (2020.01); *B06B 3/00* (2013.01); *B06B 2201/76* (2013.01)

(58) Field of Classification Search
CPC ... A61C 5/50; A61K 6/69; A61K 6/54; A61K 6/15; B06B 3/00; B06B 2201/76
USPC ...................................................... 433/228.1
See application file for complete search history.

(56) References Cited

U.S. PATENT DOCUMENTS

| | | | | |
|---|---|---|---|---|
| 5,244,933 A | * | 9/1993 | Eidenbenz | A61C 5/00 522/3 |
| 2007/0231772 A1 | * | 10/2007 | Jefferies | A61C 5/50 433/81 |
| 2009/0191506 A1 | | 7/2009 | Clark | |
| 2011/0143305 A1 | * | 6/2011 | Wagner | A61C 19/063 433/29 |
| 2011/0189627 A1 | * | 8/2011 | Gharib | A61C 5/50 433/29 |
| 2013/0122455 A1 | * | 5/2013 | Simons | A61C 5/50 433/32 |
| 2014/0212831 A1 | * | 7/2014 | Wagner | A61C 5/55 433/29 |
| 2015/0230900 A1 | | 8/2015 | Gente et al. | |
| 2017/0215992 A1 | * | 8/2017 | Clark | A61C 5/55 |
| 2020/0046459 A1 | * | 2/2020 | Ng | A61C 5/50 |

OTHER PUBLICATIONS

Baroudi et al., "Improving Composite Resin Performance Through Decreasing its Viscosity by Different Methods," The Open Dentistry Journal, 2015; 9:235-242.

(Continued)

*Primary Examiner* — Matthew M Nelson
(74) *Attorney, Agent, or Firm* — Nath, Goldberg & Meyer; Richard C. Litman

(57) ABSTRACT

The endodontic point containing ultrasonic deformable material is a filler for root canal therapy that decreases in viscosity when subjected to ultrasonic waves. Once the point is inserted into a prepared tooth space, such as a prepared and cleaned root canal, the point is subjected to ultrasonic waves. The ultrasonic waves cause the viscosity of the point to lower, thus allowing the point to flow into voids in the tooth space and allow air to escape from the voids. The point then hardens and remains in the shape acquired when at low viscosity once application of the ultrasonic waves is stopped.

1 Claim, 2 Drawing Sheets

(56) References Cited

OTHER PUBLICATIONS

Wiesse et al., "Effects of Ultrasonic and Sonic Activation of Root Canal Sealers on the Push-out Bond Strength and Interfacial Adaptation to Root Canal Dentine," International Endodontic Journal, 2017; vol. 51, 11.
Barbizam et al., "Effectiveness of a silicon-based sealer for filling of simulated lateral canals" Brazilian Dental Journal, vol. 18, 2007.
Wanstien et al., "In Vitro antibacterial activity of a silicone-based endodontic sealer and two conventional sealers" Brazilian Oral Research, Feb. 23, 2016.
Zarei et al., "Comparison between gutta-percha and Resilon retreatment", Journal of Oral Science (2009), vol. 51, No. 2, pp. 181-185.
Singh et al., "Root canal obturation by ultrasonic condensation of gutta percha and an invitro investigation on the quality of obturation", Endodontology (2012), vol. 24, pp. 109-115.
Bailey et al, "Root canal obturation by ultrasonic condensation of gutta-percha. Part II: an invitro investigation of the quality of obturation", Int. Endod. J. (2004), vol. 37, No. 10, pp. 694-698 (Abstract only).
Chadgal et al., "Effect of Ultrasonic Activation of a Bioceramic Sealer on Its Radicular Push out Bond Strength—an in Vitro Study", International Journal of Research and Review (2018), vol. 5, Iss. 10, pp. 112-116.

\* cited by examiner

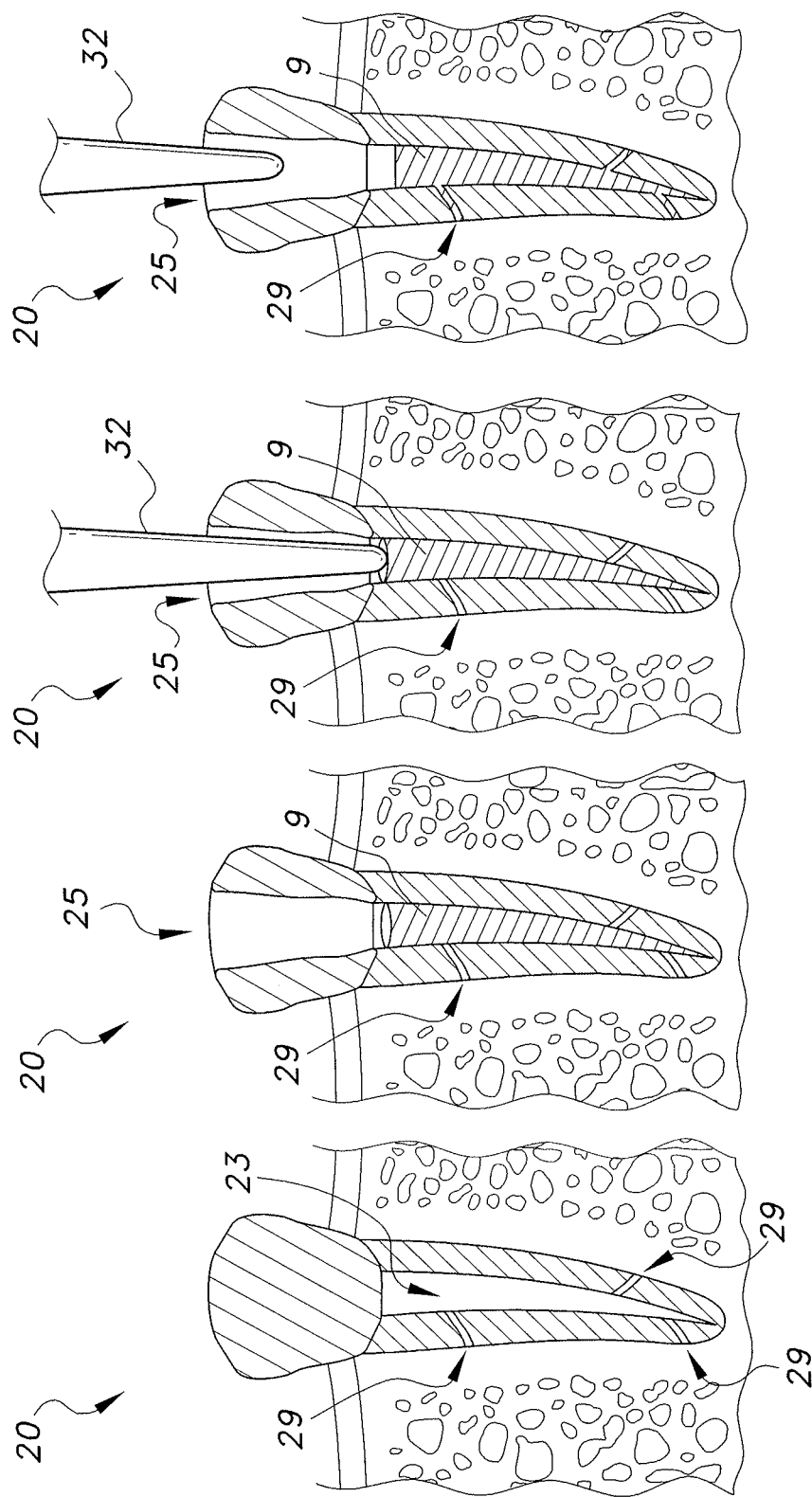

ENDODONTIC POINT CONTAINING ULTRASONIC DEFORMABLE MATERIAL

BACKGROUND

1. Field

The present disclosure relates to endodontic fillers, and in particular, to an endodontic point containing ultrasonic deformable material.

2. Description of the Related Art

Endodontics, or root canal therapy, is a part of dentistry that deals with the biology and pathology of the dental pulp and periapical tissues, as well as the prevention, diagnosis, and treatment of diseases and injuries in these tissues. One way of treating infected tissue is to remove the diseased tissue, which usually requires mechanical instrumentation of the root canal of the infected tooth. Once the diseased tissue is removed, obturation of the root canal with material that seals the canal is performed. Multiple techniques for such treatment are known in the art. These involve drilling through the outer tissue to reach the root canal space, removing the inner/diseased/infected tissue, mechanical and chemical cleaning of the canal, and then filling with a biocompatible obturation material. The tooth is then fully sealed, often using another material for the coronal part.

The obturation of the root canal space has traditionally been achieved through the use of solid, shaped material, known as "points", or "endodontic points". These are often tapered in shape, or cone shaped, reflecting the shape of the space created in the tooth, or root canal, after removal of the inner tissue. Differently sized points can be used to correspond to the size of the root canal space, which corresponds to the size and shape of the endodontic file that is used to prepare the root canal space to be filled.

Endodontic fillers provide three primary functions: (1) sealing against the ingrowth of bacteria from the oral cavity; (2) entombment of remaining microorganisms, such as bacteria; and (3) obturation to prevent infection or re-infection of the root canal space.

Gutta-percha is a known material for endodontic points. Gutta-percha refers to trees of the genius *Palaquium* and the rigid latex from the sap of these trees, although for endodontic work today, with many different additives, there are various compositional make ups of what is referred to as gutta-percha endodontic points. Resilon™ (Resilon is a trademark of Resilon Research, LLC) is a synthetic, polyester-based polymer having properties similar to gutta-percha that is also used as an obturation material in root canal therapy.

Although a great many fillers, adhesives, sealers, pastes, and other compositions and endodontic techniques have been used in root canal therapy, there still remain problems with filling all of the voids and maintaining a nearly hermetic seal of the root canal in order to protect against re-infection. Thus, an endodontic point containing ultrasonic deformable material solving the aforementioned problems is desired.

SUMMARY

The endodontic point containing ultrasonic deformable material is a filler used for root canal therapy that decreases in viscosity when subject to ultrasonic waves. Once the point is inserted into a prepared tooth space, such as a prepared and cleaned root canal, the point is subjected to ultrasonic waves. The ultrasonic waves cause the viscosity of the point to lower, thus allowing the point to flow into voids in the tooth space and allow air to escape from the voids. The point then hardens and remains in the shape acquired when at low viscosity once application of the ultrasonic waves is stopped.

These and other features of the present disclosure will become readily apparent upon further review of the following specification and drawings.

BRIEF DESCRIPTION OF THE DRAWINGS

FIG. 2A is an environmental section view of a tooth prior to preparation for receiving an endodontic point.

FIG. 2B is an environmental section view of the tooth of FIG. 2A after preparation, showing the prepared tooth space and inserted endodontic point.

FIG. 2C is an environmental section view of the tooth of FIG. 2B with an endodontic point inserted into the prepared tooth space and the head of an ultrasonic source contacting the point.

FIG. 2D is an environmental section view of the tooth of FIG. 2C after ultrasonic waves have been applied to the endodontic point and the point has filled the voids of the prepared tooth space.

Similar reference characters denote corresponding features consistently throughout the attached drawings.

DETAILED DESCRIPTION OF THE PREFERRED EMBODIMENTS

Figures 1A, 1B, 1C, 1D:
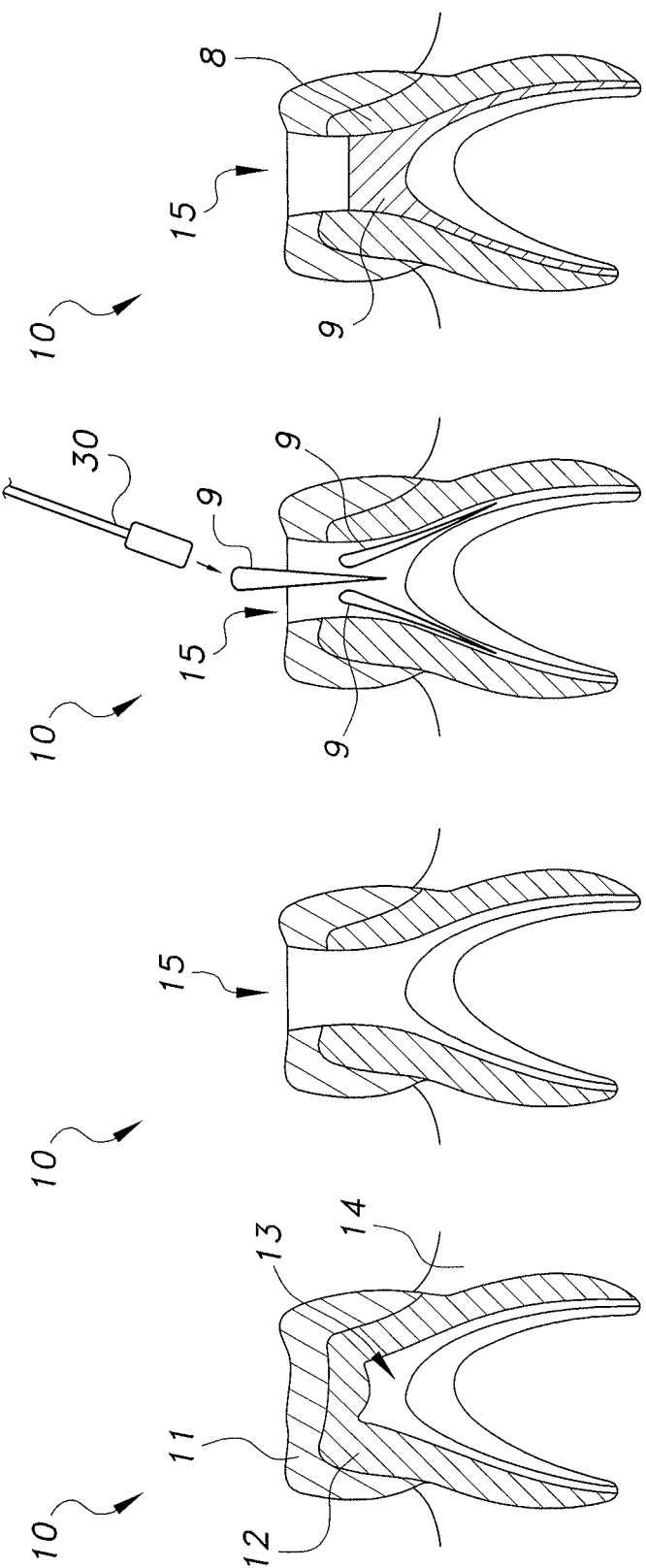
FIG. 1A is an environmental section view of a tooth prior to preparation for receiving an endodontic point.
FIG. 1B is an environmental section view of the tooth of FIG. 1A after preparation showing the prepared tooth space.
FIG. 1C is an environmental section view of the tooth of FIG. 1A with endodontic points loosely inserted into the prepared tooth space.
FIG. 1D is an environmental section view of the tooth of FIG. 1C after ultrasonic waves have been applied to the endodontic points, showing the points merged together and filling the voids of the prepared tooth space.

The term "point" or "endodontic point" is used to describe a filler material or element suitable for use in endodontic treatment, i.e., to fill a space in a tooth. The point may be any shape suitable for insertion into a tooth or, for example, the prepared root canal of a tooth, for endodontic treatment. Suitably, the point will be a solid or semi-solid at room temperature. The points may define a tapered shape, a wedge shape, or a cone shape, in part or as a whole. The points may come in different sizes and shapes, as required, suitable for insertion in the tooth. Typically these sizes will correspond to the size of dental drill bits or burrs, thus corresponding to the size and/or shape of the mechanically made bore/hole in the tooth. Similarly, the endodontic points will correspond to or match the taper and size of a rotary file or other mechanical instrument that is used to prepare the root canal or tooth space. In some embodiments, the endodontic points will correspond to the standard sizes of the industry. The points may be shaped to aid packing with other points or filler material. The points may be used alone to fill a tooth space, or may be used with a number of other points to fill a tooth space, such as a prepared tooth root canal.

Embodiments of the endodontic point containing ultrasonic deformable material 9, shown in FIG. 1A-2D, may include any suitable material that is ultrasonically deformable or sonic-activated. In other words, the point 9 may include a material that deforms when exposed to ultrasonic energy or deforms when subject to ultrasound waves for a suitable period of time. Preferably, the point 9 comprises ultrasonic deformable material that is ultrasonically deformable when positioned within the tooth, for example, in the root canal space after preparation for endodontic treatment.

The ultrasonic deformable materials may be deformable by a range of ultrasonic frequencies and intensities. Some embodiments of the point may be deformable by ultrasonic waves having frequencies that are in the range of, but not limited to, 2.5 MHz to 3.5 MHz, 2.75 MHz to 3.25 MHz, 10 kHz to 75 kHz, or 15 kHz to 70 kHz.

Ultrasound may be applied continuously or intermittently during a procedure. In some embodiments, the ultrasound may be used for only a few seconds to deform the point 9. Exemplary times for exposure to the ultrasound may be 10 seconds, 15 seconds, 20 seconds, 30 seconds, between 10 and 20 seconds, between 5 and 25 seconds, between 7 and 35 seconds, less than 30 seconds, or less than 60 seconds.

Power refers to the total amount of vibrational energy being applied over the course of the treatment and is often expressed in terms of "watts". Any range of power that allows the deformation of the ultrasonic deformable point 9 may be used. In some embodiments, the power will be low. In other embodiments, a strong ultrasound exposure for a short period of time may be used. The power of the ultrasound may be in the range of 0 to 22 Watts.

Intensity of the ultrasound refers to the total amount of vibrational energy being delivered per unit area, which is usually given in terms of, "watts per square centimeter ($W/cm^2$)". Any intensity that enables the point 9 to deform adequately can be used. In some embodiments, the intensity may be in the range of $0.5 \ W/cm^2$ to $2.5 \ W/cm^2$, $1 \ W/cm^2$ to $2.5 \ W/cm^2$, $1.5 \ W/cm^2$ to $2.5 \ W/cm^2$, $1.75 \ W/cm^2$ to $3 \ W/cm^2$, $2.1 \ W/cm^2$ to $3 \ W/cm^2$, or $2.5 \ W/cm^2$ to $3.5 \ W/cm^2$.

The four factors above, frequency, time, power, and intensity, provide numerous combinations. Some embodiments may select from the above ranges for time, frequency, power and intensity to give various amounts of ultrasound exposure, while other ranges may also be used, since the present disclosure is not limited to these disclosed ranges only. In some embodiments, the combination of time, frequency, power and intensity used will deform the endodontic point sufficiently to enable the endodontic point to reach into the voids of the tooth space and/or root canal while not completely denaturing the material of the point. This enables the endodontic point to reach into the voids as mentioned, but without going through the apical foramen and into the subapical space. Some endodontic points of the present disclosure and related techniques may allow control of the swelling of the endodontic point, thus improving filling of the tooth space and/or root canal.

The endodontic point containing ultrasonic deformable material may include any material that is ultrasonically deformable. In some embodiments, the endodontic point of the present disclosure comprises a swellable ultrasonic deformable material. When exposed to, or subjected to, ultrasound the swellable ultrasonic deformable material swells and/or deforms in shape. Swells or swellable is intended to signify an increases in size or volume. Alternatively, swells or swellable may signify deformation in shape and/or structure, where the volume of the material stays the same, but the deformation causes the material to be forced into unoccupied voids. In other words the shape of the ultrasonic swellable material may be increased in size or volume, or may just appear to do so as it deforms in shape and/or structure while the actual volume of the material may or may not remain the same. In some embodiments, the actual volume will remain the same when exposed to ultrasound and after exposure to prevent the possible negative effects discussed above.

The ultrasonic deformable material may not be completely dissolved or denatured when exposed or subject to ultrasound. In some embodiments, the endodontic point containing ultrasonic deformable material may be in a deformed or flow state for typically 3 to 6 seconds after exposure to ultrasound, although these times may vary. Remaining in a flow state for 3 to 6 seconds may enable the endodontic point to flow or spread into the voids of the tooth without going through the apical foramen into the subapical space. The endodontic point containing ultrasonic deformable material may provide control of the swelling, resulting in improved filling of the tooth space and/or root canal. The endodontic point containing ultrasonic deformable material helps reduce the risk of material (such as the endodontic point, cement, or sealer) going through the apical foramen and reaching the subapical space.

The endodontic points may be deformable to an extent that eases insertion of the endodontic point into the root canal prepared for endodontic treatment, i.e., the space of the root canal inside the tooth. In some embodiments, this space may be created by mechanical drill or burr. In some instances the space may be cone-shaped. However, the endodontic point may be used in a space having any shape.

The ultrasonic deformable material may change from a solid or semi-solid structure to a semi-solid or liquid state when exposed or subjected to ultrasound. Accordingly, the ultrasonic deformable material may decrease in viscosity when subjected or exposed to ultrasound. In some embodiments, the ultrasonic deformable material may decrease in viscosity by 5%, 10%, 15%, 20%, 25%, 40%, 50%, 60%, 70%, 75%, or 80% when exposed or subjected to ultrasound. In some embodiments, the ultrasonic deformable material may decrease in viscosity in the range of 5 to 25%, 10 to 35%, 15 to 45%, 10 to 50%, 10% to 80%, or 5 to 75% when exposed ultrasound, relative to the solid or semi-solid state when not exposed to ultrasound. Ultimately it is the endodontic point, not just one composition of it, which is important to decrease in viscosity. Some embodiments of the endodontic point may decreases in viscosity by 5%, 10%, 15%, 20%, 25%, 40%, 50%, 60%, 70%, 75%, or 80% when exposed or subjected to ultrasound, relative to the typical solid or semi-solid state when the ultrasonic deformable point is not exposed to or subjected to ultrasound. Similarly, some embodiments of the endodontic point may decrease in viscosity in the range of 5 to 25%, 10 to 35%, 15 to 45%, 10 to 50%, 10% to 80%, or 5 to 75% over the solid or semi-solid state relative to the state when not exposed or subjected to ultrasound.

The endodontic point may be deformable when subjected to ultrasound to the point where it spreads into voids, crevices/dentine tubules, and similar structures in the prepared space and/or root canal. In some embodiments, the endodontic point may remain deformed, or in a flow state for at least 3 to 6 seconds after exposure to the ultrasound. This time period may vary and can include the ranges of 2 to 7 seconds, 3 to 7 seconds, 4 to 10 seconds, or 2 to 20 seconds. When deformed, the point may remove air from the root canal and fills voids or crevices such as dentine tubules. The deformable nature of the endodontic point allows air to escape as the point is being inserted or manipulated, unlike points which remain solid or semi-solid.

The endodontic point may be quickly deformable when subjected to ultrasound. For example, the point may deform immediately or as immediately as possible when subjected to ultrasound. Also, the ultrasonic deformable materials used in the point may be reversible or partly reversible in nature, meaning that once deformed, or deformable, or swollen, or in a more liquid type of state when subjected to ultrasound, these materials will revert back to solid or semi-solid materials in normal conditions. Thus, the ultrasonic deformable material of the point may not retain a deformed structure, or a more liquid type structure, forever, or for very long, once subjected to ultrasound. In some embodiments, the ultrasonic deformable material of the point will be shape-retaining when not exposed to ultrasound. Thus, after exposure to ultrasound, the point will harden up and remain present in the voids of the root canal and/or prepared tooth space wall, and still retain the shape created when the point was deformed by ultrasound. In some embodiments, the point will remain in a deformed flow state after exposure to ultrasound has stopped for times in the range of 2 to 20 seconds, 3 to 6 seconds, 2 to 7 seconds, or 2 to 12 seconds.

In some embodiments the ultrasonic deformable material of the point may include gutta-percha, or be derived from gutta-percha. The gutta-percha used in the present disclosure may be in the Alpha or Beta forms, each of which has slightly different properties. The total gutta-percha portion of the ultrasonic deformable material may be 90 to 99%, or 85 to 95%, or 70 to 80% or 70 to 75% or 50 to 90%. The total gutta-percha portion of the endodontic point may be 90 to 99%, or 85 to 95%, or 70 to 80% or 70 to 75% or 50 to 90%.

In some embodiments, the endodontic point may comprise Resilon™ (trademark of Resilon Research, LLC). Resilon is a thermoplastic synthetic polymer often used with heat for softening. In some embodiments, the endodontic point may comprise bioceramics.

In some embodiments, the ultrasonic deformable material of the point may include silicon, be silicon-based, or be silicon-based gutta-percha. The ultrasonic deformable material may be silicon-based gutta-percha, such as, Gutta-Flow, or Roeke Seal, or Lee Endo-Fill. The ultrasonic deformable material may comprise a mixture of silicon and gutta-percha. The mixture of silicon to gutta-percha used in the point may be in the ratio of 1 to 2, 1 to 3, 1 to 4, 1 to 5, 5 to 1, 4 to 1, 3 to 1, 2 to 1, or 1 to 1, respectively. The total silicon portion of the ultrasonic deformable material may be in the range of 90 to 99%, 85 to 95%, 70 to 80%, 70 to 75%, or 50 to 90%. The total silicon portion of the endodontic point may be in the range of 90 to 99%, 85 to 95%, 70 to 80%, 70 to 75%, or 50 to 90%.

The endodontic point containing ultrasonic deformable material may include endodontic points comprising gutta-percha, Resilon, or silicon, silicon-derived materials, or other rubbery-type materials. It was previously thought that such materials would not be capable of being deformable under ultrasound, as they were too rubbery in physical nature, and that the ultrasound would permanently destroy the structure of these products. However, the presently disclosed combinations of materials in conjunction with the presently disclosed methods have been found to resist destruction when being used as endodontic fillers.

Embodiments of the endodontic points may also include agents or medicaments that help healing, reducing loss of blood, reduce pain, or kill or inhibit microorganisms, e.g., bacteria. For example, the endodontic points may include hemostatic agents, anti-microbial agents, anti-inflammatory agents, calcium hydroxide, chlorhexidine, and/or iodoform. The points may also include dyes or metal salts, such as zinc oxide, for color and radiographic contrast. Accordingly, the endodontic point may be substantially opaque to X-ray radiation to facilitate the location and identification of the endodontic point to a dental professional.

An embodiment of a method or system for treating a tooth 10 with an ultrasonic deformable material is shown in FIGS. 1A-1D. A tooth 10 requiring treatment, as shown in FIG. 1A, has enamel 11, dentin 12, a root canal 13 (which, in this example, is infected tissue) and gums 14. A mechanical apparatus such as a drill or burr, may be used to drill through a portion of the healthy enamel and dentine to reach the root canal, creating an access cavity. The root canal and soft tissue is then largely removed, leaving a prepared tooth space 15, as seen in FIG. 1B. The prepared tooth space 15 may be rinsed or washed one or more times to remove as much loose tissue and debris as possible, sterilized to remove or reduce the number of microorganisms, and dried to remove moisture. Once fully prepared for receiving the ultrasonic deformable point 9, one or more endodontic points 9 are inserted into the tooth space 5, substantially filling the tooth space 15, as seen in FIG. 1C. The endodontic points 9 may be loosely filling the prepared tooth space 15. The endodontic points 9 are then subjected to ultrasound from an ultrasonic source 30, which causes endodontic points 9 to change in structure to be more fluid in nature. The fluid nature of the points 9 allows the points 9 to spread into voids of the root canal wall and merge together to form a singular filler 8. After exposure to ultrasound has stopped, the endodontic points 9 harden (become more solid in nature) and remain in the deformed shape, occupying the voids of the tooth space 15 wall. In some embodiments, an upper portion of the prepared tooth space 15 may remain void of the point 9 material to provide for an additional a cap of a harder material that can resist the wear of a functioning tooth. In some embodiments, the cap may be a sealer. The endodontic point 9 may be of a composition that aids in adherence to the cap.

FIGS. 2A, 2B, 2C, and 2D show an embodiment of treatment using only one endodontic point 9 to substantially fill the prepare root canal 23 or tooth space 25. FIG. 2A shows the tooth 20 before treatment, including the root canal 23 and voids 29. A prepared tooth space 25 is created by mechanical creating a tooth access cavity and removing a portion of the inner tissue, leaving the prepared tooth space 25 open to the mouth, as shown in FIG. 2B. The prepared tooth space 25 may optionally be cleaned, washed, rinsed or sterilized, etc., as explained above. An endodontic point 9 is inserted into the root canal 23 area of the prepared tooth space 25, and the transmitting head of an ultrasonic source 32 is positioned in contact with the endodontic point 9 and held in position for a desired time while the endodontic point 9 is subjected to ultrasound, as seen in FIG. 2C. While the endodontic point 9 is subject to ultrasound, it deforms and swells or spreads into the voids 29, thus filling the voids 29. The transmitting head of the ultrasound source 32 is then removed, leaving the endodontic point 9 filling the tooth space 25, which includes the root canal 23 and voids 29 in the wall of the tooth space 25. In this embodiment, the endodontic point 9 is sized and shaped to correspond or match the shape of the mechanical drill or burr head so that the endodontic point 9 fits well and does not require much deformation to swell or spread into the voids 29 of the tooth space 25 walls. Minimal or no material of the endodontic point passes into the subapical space of the tooth.

The ultrasonic source 30 may be any suitable source able to deliver ultrasound to the desired position, the tooth area, or one or more endodontic points. The ultrasonic source 30 may have a relatively small ultrasonic head 32 for localising the ultrasound to a small area at any one time. The source 30 may also be suitably sized to easily fit into a patient's mouth.

During use, the ultrasonic source 30 may be placed in contact with a portion of at least one of the endodontic points 9. Other endodontic points 9 may be in contact with the at least one endodontic point 9 in contact with the ultrasonic source. In some instances, the ultrasonic source 30 may be in contact with the hard or soft tooth tissue when subjecting the endodontic points 9 to ultrasound. By the term "in contact with" this is not necessarily limited to direct contact, but includes indirect contact, for example, when a gel or other form of liquid or intermediate substance is used to aid ultrasound reaching the desired target.

Deformation of the endodontic point 9 may be controlled by placing the source 30 of the ultrasound at a particular end of the endodontic point 9, causing greater deformation of the endodontic point 9 at the end where the ultrasound is in contact with the endodontic point 9. Controlling deformation of the endodontic point 9 can prevent or minimize deformation of the point 9 at the apical foramen end, thus minimising or preventing any material from going through the apical foramen into the apical space, while allowing voids further away from the apical foramen to be filled.

With exposure to the ultrasound, the endodontic points 9 deform and decrease in viscosity so that a portion of the endodontic points 9 are able to fill small dentine tubules 29 and other small crevices in the walls of the tooth space and/or tooth tissue. When more than one endodontic point 9 is used, exposure to the ultrasound causes the endodontic points 9 to merge together, knot, or entwine so that the individual endodontic points are hard or impossible to distinguish. Both the entering of the dentine tubules/crevices 29 and the merging of endodontic points 9 aid in holding the endodontic points 9 in the tooth space 15, 25. This may relieve entirely, or proportionally, the required amount of cement and/or sealer that would traditionally be required. By reaching into small crevices, such as dentine tubules 29, the void spaces in the tooth that can harbor microorganisms are minimized. In addition, as the endodontic points 9 are in a liquid or semi-solid state when flowing into the small crevices and dentine tubules, air is able to escape out of the tooth space 15, 25 and is not blocked, as may occur with traditional solid endodontic points 9.

Some embodiments may be furnished in the form of endodontic systems or kits that comprise endodontic points 9 as described herein. These kits and systems may also comprise an ultrasonic source 30.

It is to be understood that the endodontic point containing ultrasonic deformable material is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of treating a tooth, consisting of the steps of:
   removing a portion of a tissue of the tooth to form a tooth space, wherein the tooth space includes a prepared root canal;
   providing a single endodontic point comprising an ultrasonic deformable material, the ultrasonic deformable material having a predetermined initial viscosity;
   placing into the tooth space the single endodontic point while at the predetermined initial viscosity, wherein the single endodontic point substantially fills the prepared root canal;
   after filling the prepared root canal, applying only ultrasonic waves to the single endodontic point to cause the predetermined initial viscosity of the endodontic point to decrease, wherein the ultrasonic waves have a frequency in the range of 15 kHz to 3.5 MHz and applied to the single endodontic point for a time in the range of 3 to 6 seconds; and
   stopping application of the ultrasonic waves to cause the viscosity of the endodontic point to increase, wherein the point returns to the predetermined initial viscosity after application of the ultrasonic waves has stopped.

* * * * *